(12) United States Patent
Donovan et al.

(10) Patent No.: US 9,206,411 B2
(45) Date of Patent: Dec. 8, 2015

(54) **STAPHYLOCOCCAL PHAGE2638A ENDOLYSIN AMIDASE DOMAIN IS LYTIC FOR *STAPHYLOCOCCUS AUREUS***

(75) Inventors: David M. Donovan, Baltimore, MD (US); Igor V. Abaev, Obelensk (RU)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/495,536

(22) Filed: Jun. 13, 2012

(65) Prior Publication Data

US 2013/0336954 A1    Dec. 19, 2013

(51) Int. Cl.
| | |
|---|---|
| *C12N 9/80* | (2006.01) |
| *C12N 15/52* | (2006.01) |
| *C12N 1/11* | (2006.01) |
| *C07K 14/005* | (2006.01) |
| *A01P 1/00* | (2006.01) |
| *A61L 2/16* | (2006.01) |
| *A61K 38/00* | (2006.01) |

(52) U.S. Cl.
CPC ............... *C12N 9/80* (2013.01); *C07K 14/005* (2013.01); *C12N 15/52* (2013.01); *C12Y 305/01028* (2013.01); *A61K 38/00* (2013.01); *A61L 2/16* (2013.01); *C12N 2795/10322* (2013.01); *C12N 2795/10332* (2013.01); *C12N 2795/10333* (2013.01)

(58) Field of Classification Search
None
See application file for complete search history.

(56) References Cited

FOREIGN PATENT DOCUMENTS

WO    WO 2012150858 A1 * 11/2012 ............... C12N 9/36

OTHER PUBLICATIONS

Catalão et al., A second endolysin gene is fully embedded in-frame with the lysA gene of mycobacteriophage Ms6, PLoS One, 2011, 6, e20515.*
Starmer et al., Predicting Shine-Dalgarno sequence locations exposes genome annotation errors, PLoS Computational Biology, 2006, 2, e57.*
Smits et al., Coenzyme- and His-tag-induced crystallization of octopine dehydrogenase, Acta Cryst., 2008, F64, 836-39.*
pET System Manual, Novagen, 2003.*
GenBank Reference Sequence NC_007051.1, 2007, www.ncbi.nlm.nih.gov.*
Becker et al., LysK CHAP endopeptidase domain is required for lysis of live staphylococcal cells, FEMS Microbiol. Lett., 2009, 294 52-60.*
GenBank, Accession No. NC_007051.1, 2007, www.ncbi.nlm.nih.gov.*
Guo et al., ZCURVE_V: a new self-training system for recognizing protein-coding genes in viral and phage genomes, BMC Bioinformatics, 2006, 7, 9.*

* cited by examiner

*Primary Examiner* — Rebecca Prouty
*Assistant Examiner* — Todd M Epstein
(74) *Attorney, Agent, or Firm* — John D. Fado; Evelyn M. Rabin

(57) ABSTRACT

*Staphylococcus aureus* is notorious for developing resistance to virtually all antibiotics to which it is exposed. Staphylococcal phage 2638A endolysin is a peptidoglycan hydrolase that is lytic for *S. aureus* when exposed externally, making it a new antimicrobial candidate. It shares a common protein organization with over 40 other staphylococcal peptidoglycan hydrolases: a CHAP endopeptidase domain, a mid-protein amidase 2 domain and a C-terminal SH3b cell wall binding domain. It is the first phage endolysin reported with a cryptic translational start site between the CHAP and amidase domains. Deletion analysis indicates that the amidase domain confers most of the lytic activity and requires the full SH3b domain for maximal activity. It is common for one domain to demonstrate dominant activity over another; however, the phage 2638A endolysin is the first to show high amidase domain activity dominant over the N-terminal CHAP domain, an important finding for targeting novel peptidoglycan bonds.

8 Claims, 5 Drawing Sheets
(2 of 5 Drawing Sheet(s) Filed in Color)

```
                            SEQUENCE LISTING

<160> NUMBER OF SEQ ID NOS: 34

<210> SEQ ID NO 1
<211> LENGTH: 1485
<212> TYPE: DNA
<213> ORGANISM: Artificial Sequence
<220> FEATURE:
<223> OTHER INFORMATION: Mutated Phage 2638a

<400> SEQUENCE: 1
atgctaactg ctattgacta tcttacgaaa aaaggttgga aaatatcatc tgaccctcgc      60
acttacgatg gttaccctaa aaactacggc tacagaaatt accatgaaaa cggcattaat     120
tatgatgagt tttgtggtgg ttatcataga gcttttgatg tttacagtaa cgaaactaac     180
gacgtgcctg ctgttactag cggaacagtt attgaagcaa acgattacgg taattttggt     240
ggtacattcg ttattagaga cgctaacgat aacgattgga tatgtgggca tctacaacgt     300
ggctcaatgc gatttgttgt aggcgacaaa gtcaatcaag gtgacattat tggtttacaa     360
ggtaatagca actattacga caatcctatg agtgtacatt tacatttaca attacgccct     420
aaagacgcaa agaaagatga aaaatcacaa gtatgtagtg gtttggctat ggaaaaatat     480
gacattacaa atttaaatgc taaacaagat aaatcaaaga atgggagcgt gaaagagctc     540
aaacatatct attcaaacca tattaaaggt aacaagatta cagcaccaaa acctagtatt     600
caaggtgtgg tcatccacaa tgattatggt agtatgacac ctagtcaata cttaccatgg     660
ttatatgcac gtgagaataa cggtacacac gttaacggtt gggctagtgt ttatgcaaat     720
agaaacgaag tgctttggta tcatccgaca gactacgtag agtggcattg tggtaatcaa     780
tgggcaaatg ctaacttaat cggatttgaa gtgtgtgagt cgtatcctgg tagaatctcg     840
gacaaattat tcttagaaaa tgaagaagcg acattgaaag tagctgcgga tgtgatgaag     900
tcgtacggat taccagttaa tcgcaacact gtacgtctgc ataacgaatt cttcggaact     960
tcttgtccac atcgttcgtg ggacttgcat gttggcaaag gtgagcctta cacaactact    1020
aatattaata aaatgaaaga ctacttcatc aaacgcatca acattatta tgacggtgga    1080 aagctagaag taagcaaagc agcaactatc aaacaatctg acgttaagca agaagttaaa    1140
aagcaagaag caaaacaaat tgtgaaagca acagattgga aacagaataa agatggcatt    1200
tggtataaag ctgaacatgc ttcgttcaca gtgacagcac cagagggaat tatcacaaga    1260
tacaaaggtc cttggactgg tcacccacaa gctggtgtat tacaaaaagg tcaaacgatt    1320
aaatatgatg aggttcaaaa atttgacggt catgtttggg tatcgtggga aacgtttgag    1380
ggcgaaactg tatacatgcc ggtacgcaca tgggacgcta aaactggtaa agttggtaag    1440
```

```
ttgtggggcg aaattaaact cgagcaccac caccaccacc actga            1485
```

<210> SEQ ID NO 2
<211> LENGTH: 1071
<212> TYPE: DNA
<213> ORGANISM: Phage 2638a

<400> SEQUENCE: 2

```
cgccctaaag acgcaaagaa agatgaaaaa tcacaagtat gtagtggttt ggctatggaa     60
aaatatgaca ttacaaattt aaatgctaaa caagataaat caaagaatgg gagcgtgaaa    120
gagttgaaac atatctattc aaaccatatt aaaggtaaca agattacagc accaaaacct    180
agtattcaag gtgtggtcat ccacaatgat tatggtagta tgacacctag tcaatactta    240
ccatggttat atgcacgtga gaataacggt acacacgtta acggttgggc tagtgtttat    300
gcaaatagaa acgaagtgct tggtatcat ccgacagact acgtagagtg gcattgtggt    360
aatcaatggg caaatgctaa cttaatcgga tttgaagtgt gtgagtcgta tcctggtaga    420
atctcggaca aattattctt agaaaatgaa gaagcgacat gaaagtagc tgcggatgtg    480
atgaagtcgt acggattacc agttaatcgc aacactgtac gtctgcataa cgaattcttc    540
ggaacttctt gtccacatcg ttcgtgggac ttgcatgttg gcaaaggtga gccttacaca    600
actactaata ttaataaaat gaaagactac ttcatcaaac gcatcaaaca ttattatgac    660
ggtggaaagc tagaagtaag caaagcagca actatcaaac aatctgacgt taagcaagaa    720
gttaaaaagc aagaagcaaa acaaattgtg aaagcaacag attggaaaca gaataaagat    780
ggcatttggt ataagctga acatgcttcg ttcacagtga cagcaccaga gggaattatc    840
acaagataca aggtcccttg gactggtcac ccacaagctg gtgtattaca aaaaggtcaa    900
acgattaaat atgatgaggt tcaaaaattt gacggtcatg tttgggtatc gtgggaaacg    960
tttgagggcg aaactgtata catgccggta cgcacatggg acgctaaaac tggtaaagtt   1020
ggtaagttgt ggggcgaaat taaactcgag caccaccacc accaccactg a            1071
```

<210> SEQ ID NO 3
<211> LENGTH: 948
<212> TYPE: DNA
<213> ORGANISM: Phage 2638a

<400> SEQUENCE: 3

```
atgaaacata tctattcaaa ccatattaaa ggtaacaaga ttacagcacc aaaacctagt     60
attcaaggtg tggtcatcca caatgattat ggtagtatga cacctagtca atacttacca    120
tggttatatg cacgtgagaa taacggtaca cacgttaacg gttgggctag tgtttatgca    180
aatagaaacg aagtgctttg gtatcatccg acagactacg tagagtggca ttgtggtaat    240
caatgggcaa atgctaactt aatcggattt gaagtgtgtg agtcgtatcc tggtagaatc    300
tcggacaaat tattcttaga aaatgaagaa gcgacattga agtagctgc ggatgtgatg    360
aagtcgtacg gattaccagt taatcgcaac actgtacgtc tgcataacga attcttcgga    420
acttcttgtc cacatcgttc gtgggacttg catgttggca aaggtgagcc ttacacaact    480
actaatatta taaaatgaa agactacttc atcaaacgca tcaaacatta ttatgacggt    540
ggaaagctag aagtaagcaa agcagcaact atcaaacaat ctgacgttaa gcaagaagtt    600
aaaaagcaag aagcaaaaca aattgtgaaa gcaacagatt ggaaacagaa taaagatggc    660
atttggtata agctgaaca tgcttcgttc acagtgacag caccagaggg aattatcaca    720
agatacaaag gtccttggac tggtcaccca caagctggtg tattacaaaa aggtcaaacg    780
```

```
attaaatatg atgaggttca aaaatttgac ggtcatgttt gggtatcgtg ggaaacgttt    840
gagggcgaaa ctgtatacat gccggtacgc acatgggacg ctaaaactgg taaagttggt    900
aagttgtggg gcgaaattaa actcgagcac caccaccacc accactga                948
```

<210> SEQ ID NO 4
<211> LENGTH: 494
<212> TYPE: PRT
<213> ORGANISM: Artificial Sequence
<220> FEATURE:
<223> OTHER INFORMATION: Mutated Phage 2638a

<400> SEQUENCE: 4

```
Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
    130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly Asn Lys
            180                 185                 190

Ile Thr Ala Pro Lys Pro Ser Ile Gln Gly Val Ile His Asn Asp
        195                 200                 205

Tyr Gly Ser Met Thr Pro Ser Gln Tyr Leu Pro Trp Leu Tyr Ala Arg
    210                 215                 220

Glu Asn Asn Gly Thr His Val Asn Gly Trp Ala Ser Val Tyr Ala Asn
225                 230                 235                 240

Arg Asn Glu Val Leu Trp Tyr His Pro Thr Asp Tyr Val Glu Trp His
                245                 250                 255

Cys Gly Asn Gln Trp Ala Asn Ala Asn Leu Ile Gly Phe Glu Val Cys
            260                 265                 270

Glu Ser Tyr Pro Gly Arg Ile Ser Asp Lys Leu Phe Leu Glu Asn Glu
        275                 280                 285

Glu Ala Thr Leu Lys Val Ala Ala Asp Val Met Lys Ser Tyr Gly Leu
    290                 295                 300

Pro Val Asn Arg Asn Thr Val Arg Leu His Asn Glu Phe Phe Gly Thr
305                 310                 315                 320

Ser Cys Pro His Arg Ser Trp Asp Leu His Val Gly Lys Gly Glu Pro
                325                 330                 335
```

```
Tyr Thr Thr Thr Asn Ile Asn Lys Met Lys Asp Tyr Phe Ile Lys Arg
                340             345             350
Ile Lys His Tyr Tyr Asp Gly Gly Lys Leu Glu Val Ser Lys Ala Ala
            355             360             365
Thr Ile Lys Gln Ser Asp Val Lys Gln Glu Val Lys Lys Gln Glu Ala
        370             375             380
Lys Gln Ile Val Lys Ala Thr Asp Trp Lys Gln Asn Lys Asp Gly Ile
385             390             395             400
Trp Tyr Lys Ala Glu His Ala Ser Phe Thr Val Thr Ala Pro Glu Gly
                405             410             415
Ile Ile Thr Arg Tyr Lys Gly Pro Trp Thr Gly His Pro Gln Ala Gly
            420             425             430
Val Leu Gln Lys Gly Gln Thr Ile Lys Tyr Asp Glu Val Gln Lys Phe
        435             440             445
Asp Gly His Val Trp Val Ser Trp Glu Thr Phe Glu Gly Glu Thr Val
    450             455             460
Tyr Met Pro Val Arg Thr Trp Asp Ala Lys Thr Gly Lys Val Gly Lys
465             470             475             480
Leu Trp Gly Glu Ile Lys Leu Glu His His His His His His
                485             490

<210> SEQ ID NO 5
<211> LENGTH: 357
<212> TYPE: PRT
<213> ORGANISM: Phage 2638a

<400> SEQUENCE: 5

Met Arg Pro Lys Asp Ala Lys Lys Asp Glu Lys Ser Gln Val Cys Ser
1               5                   10                  15
Gly Leu Ala Met Glu Lys Tyr Asp Ile Thr Asn Leu Asn Ala Lys Gln
            20                  25                  30
Asp Lys Ser Lys Asn Gly Ser Val Lys Glu Leu Lys His Ile Tyr Ser
        35                  40                  45
Asn His Ile Lys Gly Asn Lys Ile Thr Ala Pro Lys Pro Ser Ile Gln
    50                  55                  60
Gly Val Val Ile His Asn Asp Tyr Gly Ser Met Thr Pro Ser Gln Tyr
65                  70                  75                  80
Leu Pro Trp Leu Tyr Ala Arg Glu Asn Asn Gly Thr His Val Asn Gly
                85                  90                  95
Trp Ala Ser Val Tyr Ala Asn Arg Asn Glu Val Leu Trp Tyr His Pro
            100                 105                 110
Thr Asp Tyr Val Glu Trp His Cys Gly Asn Gln Trp Ala Asn Ala Asn
        115                 120                 125
Leu Ile Gly Phe Glu Val Cys Glu Ser Tyr Pro Gly Arg Ile Ser Asp
    130                 135                 140
Lys Leu Phe Leu Glu Asn Glu Glu Ala Thr Leu Lys Val Ala Ala Asp
145                 150                 155                 160
Val Met Lys Ser Tyr Gly Leu Pro Val Asn Arg Asn Thr Val Arg Leu
                165                 170                 175
His Asn Glu Phe Phe Gly Thr Ser Cys Pro His Arg Ser Trp Asp Leu
            180                 185                 190
His Val Gly Lys Gly Glu Pro Tyr Thr Thr Thr Asn Ile Asn Lys Met
        195                 200                 205
Lys Asp Tyr Phe Ile Lys Arg Ile Lys His Tyr Tyr Asp Gly Gly Lys
```

```
        210                 215                 220
Leu Glu Val Ser Lys Ala Ala Thr Ile Lys Gln Ser Asp Val Lys Gln
225                 230                 235                 240

Glu Val Lys Lys Gln Glu Ala Lys Gln Ile Val Lys Ala Thr Asp Trp
                245                 250                 255

Lys Gln Asn Lys Asp Gly Ile Trp Tyr Lys Ala Glu His Ala Ser Phe
                260                 265                 270

Thr Val Thr Ala Pro Glu Gly Ile Ile Thr Arg Tyr Lys Gly Pro Trp
                275                 280                 285

Thr Gly His Pro Gln Ala Gly Val Leu Gln Lys Gly Gln Thr Ile Lys
                290                 295                 300

Tyr Asp Glu Val Gln Lys Phe Asp Gly His Val Trp Val Ser Trp Glu
305                 310                 315                 320

Thr Phe Glu Gly Glu Thr Val Tyr Met Pro Val Arg Thr Trp Asp Ala
                325                 330                 335

Lys Thr Gly Lys Val Gly Lys Leu Trp Gly Glu Ile Lys Leu Glu His
                340                 345                 350

His His His His His
                355

<210> SEQ ID NO 6
<211> LENGTH: 315
<212> TYPE: PRT
<213> ORGANISM: Phage 2638a

<400> SEQUENCE: 6

Met Lys His Ile Tyr Ser Asn His Ile Lys Gly Asn Lys Ile Thr Ala
1               5                   10                  15

Pro Lys Pro Ser Ile Gln Gly Val Val Ile His Asn Asp Tyr Gly Ser
                20                  25                  30

Met Thr Pro Ser Gln Tyr Leu Pro Trp Leu Tyr Ala Arg Glu Asn Asn
                35                  40                  45

Gly Thr His Val Asn Gly Trp Ala Ser Val Tyr Ala Asn Arg Asn Glu
                50                  55                  60

Val Leu Trp Tyr His Pro Thr Asp Tyr Val Glu Trp His Cys Gly Asn
65                  70                  75                  80

Gln Trp Ala Asn Ala Asn Leu Ile Gly Phe Glu Val Cys Glu Ser Tyr
                85                  90                  95

Pro Gly Arg Ile Ser Asp Lys Leu Phe Leu Glu Asn Glu Glu Ala Thr
                100                 105                 110

Leu Lys Val Ala Ala Asp Val Met Lys Ser Tyr Gly Leu Pro Val Asn
                115                 120                 125

Arg Asn Thr Val Arg Leu His Asn Glu Phe Phe Gly Thr Ser Cys Pro
130                 135                 140

His Arg Ser Trp Asp Leu His Val Gly Lys Gly Glu Pro Tyr Thr Thr
145                 150                 155                 160

Thr Asn Ile Asn Lys Met Lys Asp Tyr Phe Ile Lys Arg Ile Lys His
                165                 170                 175

Tyr Tyr Asp Gly Gly Lys Leu Glu Val Ser Lys Ala Ala Thr Ile Lys
                180                 185                 190

Gln Ser Asp Val Lys Gln Glu Val Lys Lys Gln Glu Ala Lys Gln Ile
                195                 200                 205

Val Lys Ala Thr Asp Trp Lys Gln Asn Lys Asp Gly Ile Trp Tyr Lys
                210                 215                 220
```

```
Ala Glu His Ala Ser Phe Thr Val Thr Ala Pro Glu Gly Ile Ile Thr
225                 230                 235                 240

Arg Tyr Lys Gly Pro Trp Thr Gly His Pro Gln Ala Gly Val Leu Gln
            245                 250                 255

Lys Gly Gln Thr Ile Lys Tyr Asp Glu Val Gln Lys Phe Asp Gly His
        260                 265                 270

Val Trp Val Ser Trp Glu Thr Phe Glu Gly Glu Thr Val Tyr Met Pro
    275                 280                 285

Val Arg Thr Trp Asp Ala Lys Thr Gly Lys Val Gly Lys Leu Trp Gly
290                 295                 300

Glu Ile Lys Leu Glu His His His His His His
305                 310                 315

<210> SEQ ID NO 7
<211> LENGTH: 30
<212> TYPE: DNA
<213> ORGANISM: Phage 2638a

<400> SEQUENCE: 7
taagaaggag atatacatat gctaactgct                                    30

<210> SEQ ID NO 8
<211> LENGTH: 24
<212> TYPE: DNA
<213> ORGANISM: Phage 2638a

<400> SEQUENCE: 8
ccttgaatac tctcgagtgg tgct                                          24

<210> SEQ ID NO 9
<211> LENGTH: 26
<212> TYPE: DNA
<213> ORGANISM: Phage 2638a

<400> SEQUENCE: 9
tctcacgtgc ctcgagccat ggtaag                                        26

<210> SEQ ID NO 10
<211> LENGTH: 25
<212> TYPE: DNA
<213> ORGANISM: Phage 2638a

<400> SEQUENCE: 10
ctgtcggatg atactcgagc acttc                                         25

<210> SEQ ID NO 11
<211> LENGTH: 25
<212> TYPE: DNA
<213> ORGANISM: Phage 2638a

<400> SEQUENCE: 11
ttacaattac gccatatgga cgcaa                                         25

<210> SEQ ID NO 12
<211> LENGTH: 24
<212> TYPE: DNA
<213> ORGANISM: Phage 2638a

<400> SEQUENCE: 12
atcaaacatc tcgaggacgg tgga                                          24
```

-continued

```
<210> SEQ ID NO 13
<211> LENGTH: 25
<212> TYPE: DNA
<213> ORGANISM: Phage 2638a

<400> SEQUENCE: 13
tccctctggc tcgagcactg tgaac                                          25

<210> SEQ ID NO 14
<211> LENGTH: 28
<212> TYPE: DNA
<213> ORGANISM: Phage 2638a

<400> SEQUENCE: 14
gtggtggtgg tgctcgagtt taatttcg                                       28

<210> SEQ ID NO 15
<211> LENGTH: 18
<212> TYPE: DNA
<213> ORGANISM: Phage 2638a

<400> SEQUENCE: 15
atcgacatat gctaactg                                                  18

<210> SEQ ID NO 16
<211> LENGTH: 23
<212> TYPE: DNA
<213> ORGANISM: Phage 2638a

<400> SEQUENCE: 16
gtggtgctcg agtttaattt cgc                                            23

<210> SEQ ID NO 17
<211> LENGTH: 26
<212> TYPE: DNA
<213> ORGANISM: Phage 2638a

<400> SEQUENCE: 17
gtgaaagagc tcaaacatat ctattc                                         26

<210> SEQ ID NO 18
<211> LENGTH: 26
<212> TYPE: DNA
<213> ORGANISM: Phage 2638a

<400> SEQUENCE: 18
gatatgtttg agctctttca cgctcc                                         26

<210> SEQ ID NO 19
<211> LENGTH: 27
<212> TYPE: DNA
<213> ORGANISM: Phage 2638a

<400> SEQUENCE: 19
gaggatcgag atctcgatcc cgcgaaa                                        27

<210> SEQ ID NO 20
<211> LENGTH: 25
<212> TYPE: DNA
<213> ORGANISM: Phage 2638a

<400> SEQUENCE: 20
cgtttagagg ccccaagggg ttatg                                          25
```

```
<210> SEQ ID NO 21
<211> LENGTH: 33
<212> TYPE: DNA
<213> ORGANISM: Phage 2638a

<400> SEQUENCE: 21
cgcgcgcgca tatgaaacat atctattcaa acc                                   33

<210> SEQ ID NO 22
<211> LENGTH: 6
<212> TYPE: PRT
<213> ORGANISM: Phage 2638a

<400> SEQUENCE: 22

Met Lys His Ile Tyr Ser
1               5

<210> SEQ ID NO 23
<211> LENGTH: 5
<212> TYPE: PRT
<213> ORGANISM: Phage 2638a

<400> SEQUENCE: 23

Lys His Ile Tyr Ser
1               5

<210> SEQ ID NO 24
<211> LENGTH: 14
<212> TYPE: DNA
<213> ORGANISM: Phage 2638a

<400> SEQUENCE: 24
aaaggaagga atta                                                        14

<210> SEQ ID NO 25
<211> LENGTH: 25
<212> TYPE: DNA
<213> ORGANISM: Phage 2638a

<400> SEQUENCE: 25
aaagaatggg agcgtgaaag agttg                                            25

<210> SEQ ID NO 26
<211> LENGTH: 13
<212> TYPE: RNA
<213> ORGANISM: Phage 2638a

<400> SEQUENCE: 26 auccuccac uag                                                          13

<210> SEQ ID NO 27
<211> LENGTH: 48
<212> TYPE: DNA
<213> ORGANISM: Phage 2638a

<400> SEQUENCE: 27
aatgggagcg tgaaagagtt gaaacatatc tattcaaacc atattaaa                   48

<210> SEQ ID NO 28
<211> LENGTH: 32
<212> TYPE: DNA
<213> ORGANISM: Artificial Sequence
<220> FEATURE:
<223> OTHER INFORMATION: Chemically Synthesized
```

-continued

```
<400> SEQUENCE: 28
cgcgcgcgca tatgaaacat atctattcaa ac                                    32

<210> SEQ ID NO 29
<211> LENGTH: 10
<212> TYPE: PRT
<213> ORGANISM: Phage 2638a

<400> SEQUENCE: 29

Met Lys His Ile Tyr Ser Asn His Ile Lys
1               5                   10

<210> SEQ ID NO 30
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 30
cctcgcactt tctcgagttt gtctag                                           26

<210> SEQ ID NO 31
<211> LENGTH: 46
<212> TYPE: DNA
<213> ORGANISM: Phage 2638a

<400> SEQUENCE: 31
gggagcgtga aagagttga acatatcta ttcaaaccat attaaa                       46

<210> SEQ ID NO 32
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 32
gtgaaagagc tcaaacatat ctattc                                           26

<210> SEQ ID NO 33
<211> LENGTH: 15
<212> TYPE: PRT
<213> ORGANISM: Phage 2638a

<400> SEQUENCE: 33

Gly Ser Val Lys Glu Leu Lys His Ile Tyr Ser Asn His Ile Lys
1               5                   10                  15

<210> SEQ ID NO 34
<211> LENGTH: 1485
<212> TYPE: DNA
<213> ORGANISM: Phage 2638a

<400> SEQUENCE: 34
atgctaactg ctattgacta tcttacgaaa aaaggttgga aaatatcatc tgaccctcgc      60
acttacgatg ttaccctaa aaactacggc tacagaaatt accatgaaaa cggcattaat     120
tatgatgagt tttgtggtgg ttatcataga gcttttgatg tttacagtaa cgaaactaac     180
gacgtgcctg ctgttactag cggaacagtt attgaagcaa acgattacgg taattttggt     240
ggtacattcg ttattagaga cgctaacgat aacgattgga tatatgggca tctacaacgt     300
```

```
ggctcaatgc gatttgttgt aggcgacaaa gtcaatcaag gtgacattat tggtttacaa    360
ggtaatagca actattacga caatcctatg agtgtacatt tacatttaca attacgccct    420
aaagacgcaa agaaagatga aaaatcacaa gtatgtagtg gtttggctat ggaaaaatat    480
gacattacaa atttaaatgc taaacaagat aaatcaaaga atgggagcgt gaaagagttg    540
aaacatatct attcaaacca tattaaaggt aacaagatta cagcaccaaa acctagtatt    600
caaggtgtgg tcatccacaa tgattatggt agtatgacac ctagtcaata cttaccatgg    660
ttatatgcac gtgagaataa cggtacacac gttaacggtt gggctagtgt ttatgcaaat    720
agaaacgaag tgctttggta tcatccgaca gactacgtag agtggcattg tggtaatcaa    780
tgggcaaatg ctaacttaat cggatttgaa gtgtgtgagt cgtatcctgg tagaatctcg    840
gacaaattat tcttagaaaa tgaagaagcg acattgaaag tagctgcgga tgtgatgaag    900
tcgtacggat taccagttaa tcgcaacact gtacgtctgc ataacgaatt cttcggaact    960
tcttgtccac atcgttcgtg ggacttgcat gttggcaaag gtgagcctta cacaactact   1020
aatattaata aaatgaaaga ctacttcatc aaacgcatca aacattatta tgacggtgga   1080
aagctagaag taagcaaagc agcaactatc aaacaatctg acgttaagca agaagttaaa   1140
aagcaagaag caaaacaaat tgtgaaagca acagattgga aacagaataa agatggcatt   1200
tggtataaag ctgaacatgc ttcgttcaca gtgacagcac cagagggaat tatcacaaga   1260
tacaaaggtc cttggactgg tcacccacaa gctggtgtat tacaaaaagg tcaaacgatt   1320
aaatatgatg aggttcaaaa atttgacggt catgtttggg tatcgtggga aacgtttgag   1380
ggcgaaactg tatacatgcc ggtacgcaca tgggacgcta aaactggtaa agttggtaag   1440
ttgtggggcg aaattaaact cgagcaccac caccaccacc actga                   1485
```

STAPHYLOCOCCAL PHAGE2638A ENDOLYSIN AMIDASE DOMAIN IS LYTIC FOR STAPHYLOCOCCUS AUREUS

BACKGROUND OF THE INVENTION

1. Field of the Invention

This invention relates to a nucleic acid encoding a functional module or domain of a particular peptidoglycan hydrolase, i.e., the phage 2638A endolysin, a protein which specifically attacks the peptidoglycan cell wall of untreated *Staphylococcus aureus* and selected coagulase negative staphylococci (for example: *S. chromogenes, S. simulans, S. epidermidis*). The invention relates in particular to a full length construct comprising the mutant 180 codon (2638A 1-180 Mut-486) and to truncated constructs encoding a full length amidase domain and the full length SH3b domain, 2638A 139-486 and 2638A 180-486) and to the functional proteins encoded by the constructs.

2. Description of the Relevant Art

The increased incidence of bacterial antibiotic resistance has led to a renewed search for novel antimicrobials. *Staphylococcus aureus* has a high negative impact worldwide as a human pathogen and also as a mastitis-causing organism based on its role in infections of dairy cattle mammary glands. *S. aureus* has a high capacity for resistance development. Resistant *S. aureus* strains exist to virtually every known antibiotic. Bacteriophage endolysins are proteins encoded by bacteriophage (viruses that infect bacteria) that help nascent phage escape their host by degrading peptidoglycan, the major structural component of bacterial cell walls. Thus, phage and host have co-evolved such that, for those species examined, no endolysin-resistant host strains have been identified (Fischetti, V. A. 2005. *Trends Microbiol.* 13:491-496), making phage endolysins candidate antimicrobials that are highly refractory to resistance development. To further ensure that our antimicrobials are refractory to resistance development, we have previously created fusion antimicrobials with three active lytic domains, based on the belief that no bacterium can evade three simultaneous, unique, synergistic activities (Donovan et al. 2009. *Biotech International* 21:6-10).

The bacterial peptidoglycans have a complex structure (sugar backbone of alternating units of N-acetyl glucosamine and N-acetyl muramic acid (NAM) residues, cross-linked by oligopeptide attachments at the NAMs). Endolysins have evolved a modular design to deal with this complexity. One protein can harbor multiple domains, each with a different peptidoglycan digestion activity. Three classes of endolysin domains have been identified thus far: the endopeptidase, glycosidase, and amidase domains (Loessner, M. J. 2005. *Curr. Opin. Microbiol.* 8: 480-487). Each catalytic domain has been localized to short protein domains (~100-200 amino acids). Any one of these domains is sufficient to lyse the bacterial target cell.

It has been reported that antibiotic treatment of mastitis is less than 50% effective (Deluyker et al. 2005. *J. Vet. Pharmacol. Ther.* 22:274-282). *S. aureus* is also a notorious human pathogen with multi-drug resistant strains plaguing clinics world wide. A new antimicrobial to combat this pathogen would be an excellent addition to the collection of current treatments. There are numerous other bacteriophage endolysins that have been reported to be active against live *S. aureus*; for example: the phage K endolysin (O'Flaherty et al. 2005. *J. Bacteriol.* 187:7161-7164; Becker et al. 2008. *FEMS Microbiol. Lett.* 287:185-191; Becker et al. 2009a. *Gene* 443: 32-41), the lys16 endolysin from the *S. aureus* phage P68 (Takac et al. 2005. *Microbiol.* 151:2331-2342), and the lysWMY endolysin from the *Staphylococcus warneri* M phage (Yokoi et al. 2005. *Gene* 351:97-108), to name a few.

Antibiotic resistance among pathogens is believed to develop, in part, through the use of broad range antibiotics, which affect not only the target pathogen, but can also select for resistance in other bacteria (e.g. commensals). The use of a highly specific antimicrobial would target fewer species, and thus is less likely to contribute to the broad range resistance development now apparent with commonly used broad range antibiotics. Bacteriophage endolysins are uniquely specific to their host (or closely related species); bacteriophage and bacterial hosts have co-evolved. It is difficult to prove that resistance cannot develop to endolysins, but to date, none has been reported and this fact alone makes this product a candidate for addition to the battery of antimicrobials available to both veterinary medicine and the clinician. If resistant strains are not produced, this would be an important antimicrobial for use and efficacy.

Thus, to manage the upsurge of drug resistant pathogenic bacteria, there is a need for new specific antimicrobial treatments. Reagents developed specifically for the relevant genera, species or substrains of concern would function as effective tools for controlling economically important diseases and therefore are ideal candidates for therapeutic treatments.

SUMMARY OF THE INVENTION

We have discovered that the nucleic acid encoding the endolysin of the staphylococcal phage 2638A comprises a cryptic translational start site in the inter-lytic domain region between the CHAP and amidase domains and that a mutation in codon 180 of the polynucleotide with the cryptic translation start site results in a full length construct comprising the mutant 180 codon (2638A 1-180 Mut-486) and expression of the construct (2638A 1-180 Mut-486) generates a full length 2638A 1-180 Mut-486 endolysin that is lytic for *Staphylococcus aureus* when exposed externally and that truncated 2638A endolysins comprising the full length amidase domain and the full length SH3 domain confer most of the lytic activity and are dominant to truncated 2638A endolysins comprising either the CHAP domain, or the CHAP domain fused to the SH3b domain.

In accordance with this discovery, it is an object of the invention to provide nucleic acid molecules encoding full length 2638A 1-180 Mut-486 endolysin resulting from mutating codon 180, a cryptic translational start site and nucleic acid molecules encoding the truncated endolysins 2638A 139-486 and 2638A 180-486 comprising the full length amidase domain and the full length SH3b domain.

An added object of the invention is to provide a nucleic acid sequence encoding 2638A endolysin or truncated 2638A endolysin polypeptides according to the invention as an encoding sequence which allows disease resistance to be imparted to the organism. It is well understood that this sequence can also be used in combination with another sequence, or sequences, encoding one or more disease resistant properties.

Another object of the invention is to provide a nucleic acid sequence encoding the uniquely active amidase domain of the 2638A endolysin or truncated 2638A endolysin polypeptides according to the invention as an encoding sequence which allows disease resistance to be imparted to the organism. It is well understood that this sequence can also be used in combination with another sequence, or sequences, encoding one or more disease resistant properties.

It is an object of the invention to provide a nucleic acid sequence encoding 2638A endolysin or truncated 2638A endolysin polypeptides according to the invention as an encoding sequence which can be expressed in the mammary glands of transgenic cattle.

It is a further object of the invention to provide a nucleic acid encoding an antimicrobial fusion protein formed from a nucleic acid encoding a functional module or domain of the 2638A endolysin, a protein which specifically attacks the peptidoglycan cell wall of untreated S. aureus and coagulase negative staphylococci in combination with nucleic acid encoding a functional module(s) or domain(s) of another endolysin(s) having a different hydrolase activity, e.g., glycosidase, amidase and endopeptidase activity.

A still further object of the invention also relates to a chimeric gene (or expression cassette) comprising an encoding sequence as well as heterologous regulatory elements in positions 5' and 3' which can function in a host organism, the encoding sequence comprising at least one nucleic acid sequence encoding an antimicrobial 2638A endolysin or a truncated 2638A endolysin.

An additional object of the invention is to provide a host organism into which the 2638A gene, or truncated gene, according to the invention can be introduced so as to produce an endolysin or truncated endolysin.

A further object of the invention is to provide a composition useful for the treatment of disease caused by bacteria for which the full length 2638A endolysin polypeptide is specific.

An added object of the invention is to provide compositions useful for the treatment of disease caused by bacteria for which the full length 2638A endolysin-derived protein having a mutation in position 180 of 2638A endolysin has enhanced, specific antimicrobial activity, given the advantageous antimicrobial activity observed with the full length 2638A endolysin protein and the preserved mutated 2638A endolysin-derived protein together.

A further object of the invention is to provide a composition useful for the treatment of disease caused by bacteria for which the truncated 2638A endolysin-derived proteins are specific.

Also part of this invention is a kit, comprising a composition for treatment of disease caused by the bacteria for which the 2638A endolysin and truncated 2638A endolysin are specific.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A. The black boxes depict the M23 peptidase domain; the grey boxes, the amidase domain; and the striped boxes, the SH3b domain. Amino acid positions are numbered. The asterisk indicates mutated amino acid 180. FIG. 1B depicts SDS PAGE (shadow bands are indicated with arrows). FIG. 1C depicts zymogram analysis. Dark bands in the zymogram gel indicate regions where the S. aureus embedded in the gel have been lysed and a zone of clearing has resulted.

FIG. 2A shows the results of the Edman degradation N-terminus protein sequence analysis of the shadow band from the SDS PAGE analysis. The underlined protein sequences were obtained. The Nde I restriction enzyme recognition sequence (CATATG) for cloning of the 2638A 180-486 PCR fragment into the pET21a multi-cloning site is underlined. The Nde I site includes the ATG start of translation for the 2638A 180-486 truncation construct. A potential Shine-Dalgarno (SD) binding site for the 3' end of the E. coli 16S rRNA sequence (UCCUCC; SEQ ID NO:32) is overlined. Predicted RNA-DNA base-pairing is indicated with vertical bars. FIG. 2B shows the Silent Primer R and Silent Primer F used in the site directed mutagenesis PCR strategy to create the 2638A 1-180Mut-486 construct that created silent mutations that exchanged the 180 TTG for a CTC codon.

DETAILED DESCRIPTION OF THE INVENTION

Figure 1:
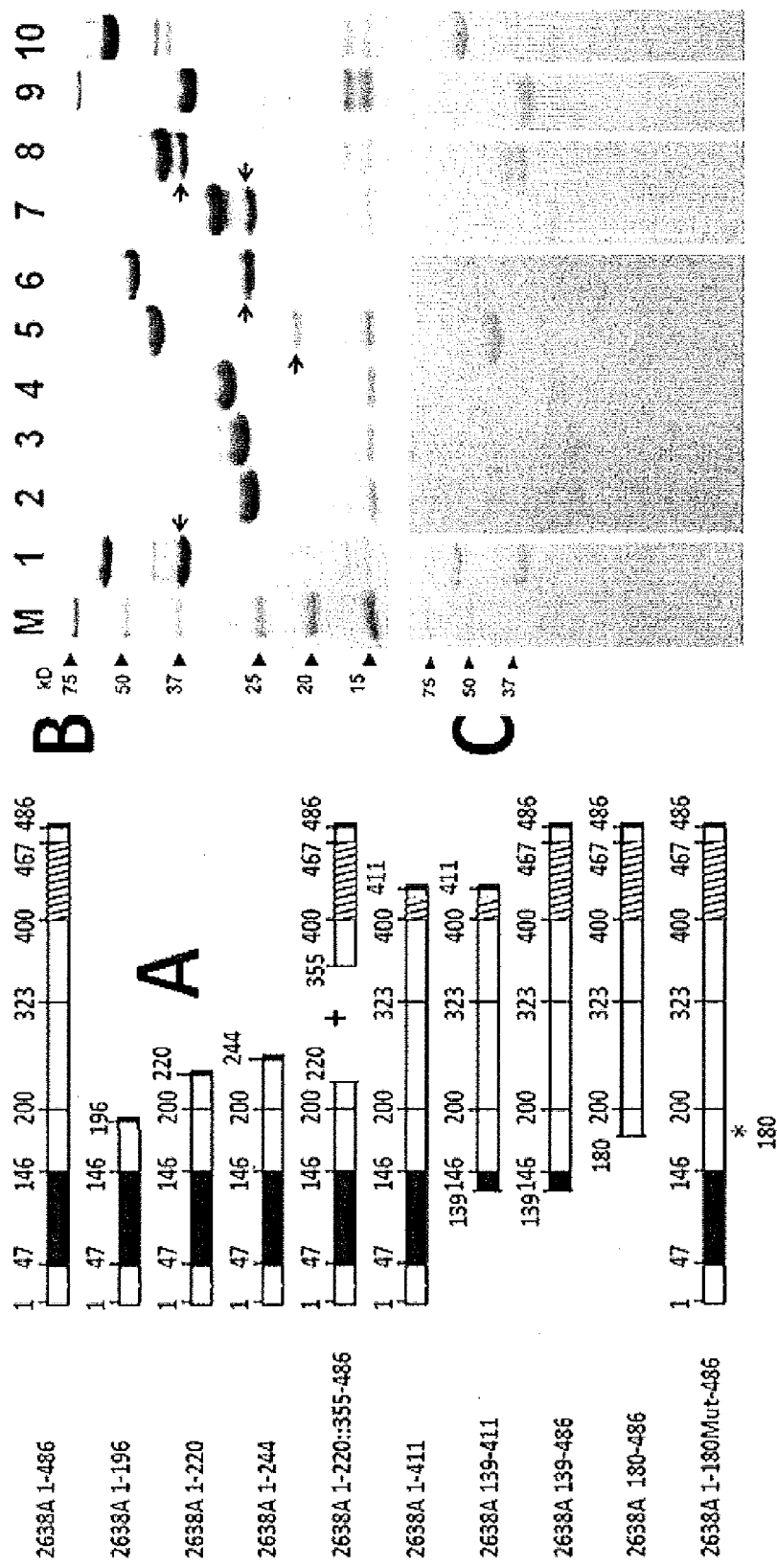
FIGS. 1A-1C are schematic representations of endolysin 2638A constructs and both SDS PAGE and Zymogram analyses depicting the purity and lytic activity of these constructs, respectively.

We are interested in identifying staphylococcal endolysins that might serve to impede the escalating development of S. aureus resistant strains. To ensure that our antimicrobials are refractory to resistance development, we have created fusion antimicrobials with three active lytic domains (Donovan et al. 2009, supra), in the belief that no bacterium can evade three simultaneous, unique, synergistic activities. To identify novel domains, we recently collated the SH3b cell wall binding domain containing staphylococcal peptidoglycan hydrolases (Becker et al. 2009a, supra) from public datasets, including many with dual lytic domains. The 486 amino acid 2638A endolysin (Genbank Accession number AAX90995) harbors an N-terminal M23 peptidase domain (retrieved from the Internet: <URL: pfam.sangerac.uk/family?acc=PF01551), a mid-protein amidase 2 domain (N-acetylmuramoyl-L-alanine amidase; retrieved from the Internet: <URL: (ebi.ac.uk/QuickGO/GTerm?id=GO:0008745), and a C-terminal SH3b_5 (SH3b) cell wall binding domain (retrieved from the Internet: <URL: pfam.sanger.ac.uk/family/PF08239) (See FIG. 1 construct 2638A 1-486). The 2638A endolysin is of interest to us because, in so far as an amino acid sequence can alter protein properties or affinities, the 2638A endolysin, as a poorly conserved member of the SH3b-containing endolysins (<50% identity), could potentially harbor novel sequences that might convey antimicrobial activity in diverse environment(s).

Phage endolysins are known to be modular in structure (Diaz et al. 1990. *Proc. Natl. Acad. Sci. U.S.A.* 87:8125-8129; Donovan et al. 2006a. *Appl. Environ. Microbiol.* 72:2988-2996; Garcia et al. 1990. *Gene* 86:81-88), and there are numerous examples where single domains are functional without the need for the second lytic domain or the cell wall binding domain (Becker et al. 2009b. *FEMS Microbiol. Lett.* 294:52-60; Donovan et al. 2006b. *Appl. Environ. Microbiol.* 72:5108-5112; Donovan et al. 2006c. *FEMS Microbiol. Lett.* 265:133-139). However, it is still important to demonstrate lysis from without for each endolysin, when considering them as antimicrobials. Toward this end, we isolated the 2638A gene from *S. aureus* 2854 (HER 1283; University Laval, Quebec, Canada) genomic DNA using PCR cloning, (primers described in Table 2, Example 2) and subcloned this fragment into pET21a (Novagen) *E. coli* expression vector (construct 2638A 1-486; FIG. 1A).

We examined, by deletion analysis, the involvement of each of the three domains of 2638A lysin during cell lysis. Deletion variants of the 2638A lysin protein were constructed to isolate each domain on a separate construct so that each domain could be assayed independently. Each deletion variant was His-tagged at the C terminus. Expression of the endolysin constructs was in *E. coli* (BL21 DE3). All constructs yielded soluble proteins that were purified via (non-Urea) NiNTA nickel column chromatography also previously described (Donovan and Foster-Frey. 2008. *FEMS Microbiol. Lett.* 287:22-33).

SDS PAGE analysis revealed >90% purity of the resultant purified proteins, except for five of the constructs that extended across the inter-domain region between the peptidase and amidase domains (2638A 1-486; 2638A 1-220::355-486; 2638A 1-411; 2638A 139-411; 2638A 139-486), see Example 3. In these five constructs, there was a second "shadow" band that was consistently co-isolated at high concentration and purity (FIG. 1B). The predicted size of the shadow band protein was consistent between those constructs that terminated at the same residue (e.g. 2638A 1-486 and 2638A 139-486 vs. 2638A 1-411 and 2638A 139-411) suggesting either a consistently favored protein degradation site or a cryptic translational start site.

All full length constructs and the shadow bands [except for 2638A 1-220::355-486] showed staphylolytic activity (zones of clearing) in the zymogram (FIG. 1C) indicating: (1) that the N-terminal M23 peptidase domain was enzymatically active with or without the SH3b cell wall binding domain and (2) the amidase domain was active with or without the full length SH3b domain, see Example 4.

In order to identify the source of the shadow band, it was extracted from the SDS gel from the full length construct 2638A 1-486 sample using standard methods and subjected to Edman degradation N-terminal protein sequencing (M-SCAN, West Chester, Pa.). The last five residues of the resultant amino acid sequence matched perfectly the residues at position 181-184 of the full length 2638A endolysin protein which was consistent with the predicted size of the shadow band from the SDS PAGE (~37 kD). The N-terminal methionine residue matched the predicted amino acid sequence of a protein expressed from a cryptic translational start site (TTG) at residue 180 thru 486 (36.3 kD), of the published DNA sequence and additional experimental evidence suggested that codon 180 encoded a translational start site.

To test this cryptic translational start site hypothesis, a ninth construct (construct 2638A 1-180Mut-486; FIG. 1A) with two silent mutations was created where the TTG codon was altered through site-directed mutagenesis to an alternative [CTC] codon that still codes for leucine but did not resemble a translational start site (Example 2). The resultant construct (2638A 1-180Mut-486; FIG. 1A) does not have a shadow band in either the SDS or zymogram gels making it very likely that our alternative translational start site hypothesis was correct. The single lytic protein product from this construct allowed us to quantify the activity of the full length 2638A endolysin.

In order to test the activity of the amidase domain together with the SH3b cell wall binding domain construct in the absence of the contaminating shadow band protein, we created a construct via PCR cloning that initiated at codon 180 (2638A 180-486; FIG. 1A and described in FIG. 2A). In the SDS PAGE (FIG. 1B), this construct expressed a single major protein band as predicted, and none of the minor contaminating bands contributed to any activity in the zymogram analysis.

The nucleic acid sequences encoding the phage 2638A endolysin-derived proteins: 2638A 1-180 Mut-486, 2638A 139-486, and 2638A 180-486 are identified by SEQ ID NO:1, SEQ ID NO:2, and SEQ ID NO:3, respectively. These sequences include the nucleotides encoding the six histidine tag required for purification. The amino acid sequence of the phage 2638A endolysin-derived protein 2638A 1-180 Mut-486 is identified by SEQ ID NO:4. The truncated endolysin proteins, 2638A 139-486 and 2638A 180-486 are identified by SEQ ID NO:5 and SEQ ID NO:6, respectively. The encoding sequences of the individual modules of the phage 2638A endolysin according to the invention can be assembled by any usual method for constructing and assembling nucleic acid fragments which are well known to those skilled in the art and widely described in the literature and illustrated especially by the use examples of the invention.

Staphylolytic activity was further characterized with two quantitative peptidoglycan hydrolase assays, the turbidity reduction assay and the plate lysis assay, as described previously (Donovan and Foster-Frey, supra).

Another subject of the invention is the use of a nucleic acid sequences encoding the phage 2638A endolysins according to the invention as encoding sequences which allow disease resistance to be imparted to the organism. It is well understood that these sequences can also be used in combination with another sequence, or sequences, encoding one or more disease resistant properties. The present invention therefore also relates to a strategy of generating a nucleic acid sequence encoding a chimeric endolysin according to the invention, this process being defined herein.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding a phage 2638A endolysin related protein (truncation or fusion) as defined above. By host organism there is to be understood any single-celled or lower or higher non-human multi-celled organism into which a phage 2638A endolysin gene according to the invention can be introduced. The regulatory elements required for expressing the nucleic acid sequence encoding a phage 2638A endolysin are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least one of the phage 2638A endolysin genes as defined hereinabove. This vector comprises, in addition, to the above phage 2638A endolysin gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the phage 2638A endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional phage 2638A endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of phage 2638A endolysin" refers to all fragments of phage 2638A endolysin that retain phage 2638A endolysin activity and function to lyse staphylococcal bacteria.

Modifications of the phage 2638A endolysin primary amino acid sequence may result in further mutant or variant proteins having substantially equivalent activity to the phage 2638A endolysin polypeptides described herein. Such modifications may be deliberate, as by site-directed mutagenesis, or may occur by spontaneous changes in amino acid sequences where these changes produce modified polypeptides having substantially equivalent activity to the phage 2638A endolysin polypeptide. Any polypeptides produced by minor modifications of the phage 2638A endolysin primary amino acid sequence are included herein as long as the biological activity of phage 2638A endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a phage 2638A endolysin polypeptide and which hybridize under stringent conditions to the phage 2638A endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have phage 2638A endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the phage 2638A endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, phage 2638A endolysin activity as described herein. Such variants may result from, for example, genetic polymorphism or from human manipulation. Biologically active variants of a native phage 2638A endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired phage 2638A endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of phage 2638A endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Bacterial Strains and Culture Conditions

The strains used include numerous *S. aureus* strains and mastitis isolates, *S. chronogenes, S. epidermidis, S. simulans* (a gift from M. Paape, USDA, Beltsville, Md.), *S. hyicus, S. warneri*, and *S. xylosus* described in Table 1.

TABLE 1

Susceptibility of multiple bacterial strains to lysis by 2638A after 1 and 3+ days.

| S. aureus. Strain | Phage 2638A Endolysin | | S. aureus. Strain | Phage 2638A Endolysin | |
|---|---|---|---|---|---|
| | day 1 | day 3+ | | day 1 | day 3+ |
| Newman | − | − | Tanji 1 | − | − |
| 305 | − | − | Tanji 2 | − | + |
| Newman sm$^r$ | − | − | Tanji 3 | − | − |
| Newman ΔtagO | +++ | +++ | Tanji 9 | − | − |
| Newman Δica | − | − | Tanji 19 | − | + |
| Newman ΔdltA | − | − | Tanji 20 | − | + |
| Newman srtA::ermB | − | − | Tanji 21 | − | (+) |
| MN8 | − | ++ | Tanji 26 | − | + |
| MN8 Δica | − | ++ | Tanji 28 | − | − |
| MN8 ΔsarA | (+) | +++ | Tanji 29 | (+) | +(+) |
| ALC 1342 | − | − | Tanji 31 | − | − |
| ANG 133 | − | − | Tanji 33 | − | + |
| ANG 144 | − | − | Tanji 47 | − | (+) |
| SA113 | + | ++ | Tanji 48 | − | + |
| SA113 ΔtagO | +++ | +++ | Tanji 49 | − | +(+) |
| SA113 ΔdltA | +(+) | ++(+) | | | |
| Reynolds (CP-) | − | − | | | |
| Reynolds (CP5) | − | − | S. chromogenes | +(+) | ++(+) |
| Reynolds (CP8) | − | − | S. epidermidis | − | + |
| NRS 382 (MRSA) | − | − | S. hyicus | − | − |
| NRS 383 (MRSA) | (+) | ++ | S. simulans | − | (+) |
| NRS 384 (MRSA) | − | (+) | S. warneri | − | − |
| NRS 385 (MRSA) | − | − | S. xylosus | − | − |

Concentrations causing a lysis zone:
− = >100 pmol;
(+) = very faint lysis zone;
+ = 100 pmol;
++ = 10 pmol;
+++ = 1 pmol The staphylococcal phage 2638A lysin gene in pET21a (EMD Biosciences, San Diego, Calif.) was cloned in *E. coli* DH5a (Invitrogen) and both full length and deletion constructs expressed in BL21 DE3 *E. coli* cells (Pritchard et al., 2007). Deletion mutants of the phage 2638A lysin protein were constructed with standard molecular techniques (FIG. 1A).

Example 2

PCR Cloning

We isolated the 2638A gene from *S. aureus* 2854 (HER 1283; University Laval, Quebec, Canada) genomic DNA using PCR cloning, (primers described in Table 2) and subcloned this fragment into pET21a (Novagen) *E. coli* expression vector (construct 2638A 1-486; FIG. 1A). The gene fragments were amplified with PCR primers (2) engineered with either an NdeI or XhoI site designed to introduce appropriate restriction enzyme sites for subcloning into pET21a. PCR products were gel purified, digested appropriately with restriction enzymes, purified over a Micro Bio Spin P30 desalting column (Bio-Rad Inc., Hercules, Calif.) and introduced into similarly digested, dephosphorylated, and gel-purified pET21a via conventional means. All constructs (FIG. 1A and Table 2) are C-terminally His-tagged with eight additional amino acid residues introduced at the C-terminus corresponding to the XhoI site (Leu-Glu) followed by six His residues. All subcloning was performed in *E. coli* DH5α (Invitrogen, Carlsbad, Calif.) for plasmid DNA isolation and sequence verification of all constructs. pET21a constructs were induced in *E. coli* BL21 (DE3) (EMD Biosciences, San Diego, Calif.).

TABLE 2

Primers used in making 2638A constructs.

| Primers | SEQ ID NO: | Sequences | Construct |
|---|---|---|---|
| 2638A NdeI-1F | 7 | 5'-TAAGAAGGAGATATACATATGCTAACTGCT | 2638A 1-486, 2638A 1-196, 2638A 1-220, 2638A 1-244 2638A 1-411, 2638A 1-220::355-486 |
| 2638A XhoI-196R | 8 | 5'-CCTTGAATACTCTCGAGTGGTGCT | 2638A 1-196 |
| 2638A XhoI-220R | 9 | 5'-TCTCACGTGCCTCGAGCCATGGTAAG | 2638A 1-220, 2638A 1-220::355-486 |
| 2638A XhoI-244R | 10 | 5'-CTGTCGGATGATACTCGAGCACTTC | 2638A 1-244 |
| 2638A NdeI-139F | 11 | 5'-TTACAATTACGCCATATGGACGCAA | 2638A 139-411, 2638A 139-486 |
| 2638A XhoI-355F | 12 | 5'-ATCAAACATCTCGAGGACGGTGGA | 2638A 1-220::355-486 |
| 2638A XhoI-411R | 13 | 5'-TCCCTCTGGCTCGAGCACTGTGAAC | 2638A 1-411, 2638A 139-411 |
| 2638A XhoI-486R | 14 | 5'-GTGGTGGTGGTGCTCGAGTTTAATTTCG | 2638A 1-486, 2638A 139-486; 2638A 1-220::355-486 |
| 2638A NdeI F | 15 | 5'-ATCGACATATGCTAACTG | 2638A 1-180Mut-486, 2638A 180-486 |
| 2638A Xho R | 16 | 5'-GTGGTGCTCGAGTTTAATTTCGC | 2638A 1-180Mut-486 |
| f2638A CTC 180 mutantF | 17 | 5'-GTGAAAGAGCTCAAACATATCTATTC | 2638A 1-180Mut-486 |
| 2638A CTC 180 mutantR | 18 | 5'-GATATGTTTGAGCTCTTTCACGCTCC | 2638A 1-180Mut-486 |
| pET21a Bgl II F | 19 | 5'-GAGGATCGAGATCTCGATCCCGCGAAA | 2638A 1-180Mut-486 |
| pET21a Sty I R | 20 | 5'-CGTTTAGAGGCCCAAGGGGTTATG | 2638A 1-180Mut-486 |
| 2638A NdeI-180F | 21 | 5'-CGCGCGCGCATATGAACATATCTATTCAAACC | 2638A 180-486 |

In this study, we examined the involvement of each of the three domains of 2638A lysin during cell lysis by deletion analysis. Deletion C-terminal His-tagged variants of the 2638A lysin protein were constructed to isolate each domain on a separate construct so that each domain could be assayed independently. Initially, seven deletion constructs were created via PCR cloning technology in pET21a (conferring a C-terminal 6×His tag) as described previously (Becker et al. 2009b, supra) using the primers in Table 2. All constructs were sequence verified (2638A 1-196; 2638A 1-220; 2638A 1-244; 2638A 1-220::355-486; 2638A 1-411; 2638A 139-411; 2638A 139-486).

Expression of the endolysin constructs was in *E. coli* (BL21 DE3). All constructs yielded soluble proteins that were purified via (non-Urea) NiNTA nickel column chromatography also previously described (Donovan and Foster-Frey. 2008. *FEMS Microbiol. Lett.* 287:22-33).

Example 3

Protein Purification and SDS Analysis

Mid log phase ($OD_{600\ nm}$ of 0.4-0.6) *E. coli* cultures harboring pET21a-derived expression vectors were grown under ampicillin selection, chilled on ice for 30 min, induced with 1 mM IPTG, and incubated with shaking for 18 h at 19° C. *Escherichia coli* harvested from 100 mL cultures were suspended in 2 mL lysis buffer (50 mM $NaH_2PO_4$, 300 mM NaCl, 10 mM imidazole, pH 8), sonicated on ice for 15×5 s pulses separated by 15 s rests, and centrifuged at 9000 g. for 30 min in a Sorvall HS4 rotor. The cleared supernatant was applied to 1 mL nickel-nitrilotriacetic acid (Ni-NTA) Agarose (nickel matrix) in a slurry and mixed gently for 1 h at 4° C. (Qiagen). The wash and elution buffer profiles were empirically determined for all constructs to be 10 mL of 10 mM imidazole, 20 mL of 20 mM imidazole and eluted into 1.2 mL of 250 mM imidazole in the same phosphate-buffered saline (50 mM $NaH_2PO_4$, 300 mM NaCl, pH 8.0). One percent of glycerol was added immediately to the eluate to avoid potential solubility problems that are known to exist for His-tagged proteins (Woestenenk et al., 2004. *J. Struc. Func. Genomics* 5:217-229). All samples were then either converted to storage buffer (10 mM Tris-Cl pH 7.5, 150 mM NaCl with 1% glycerol) via a Zeba desalting column (Pierce) that was previously converted to storage buffer or assayed directly in nickel column elution buffer with 1% glycerol. All samples were 0.22-μm filter sterilized for use in plate lysis assays. Sterilized proteins were stored at 4 or −80° C. until use. Protein concentration determinations were via a BCA Protein kit (Pierce). The purity of each preparation was determined via sodium dodecyl sulfate-polyacrylamide gel electrophoresis (SDS-PAGE).

The purified constructs and Precision Plus protein standards (Bio-Rad) were analyzed with 15% SDS-PAGE in Tris-Glycine buffer at 150 V for 1.5 h in Criterion Precast gels (Bio-Rad Inc.), according to the manufacturer's instructions. Gels were stained in Coomassie stain for 1 h and then destained for 6-18 h via conventional methods.

SDS PAGE analysis revealed >90% purity of the resultant purified proteins, except for five of the constructs that extended across the inter-domain region between the peptidase and amidase domains (2638A 1-486; 2638A 1-220:: 355-486; 2638A 1-411; 2638A 139-411; 2638A 139-486,). In these five constructs, there was a second "shadow" band that was consistently co-isolated at high concentration and purity (FIG. 1B). The predicted size of the shadow band protein was consistent between those constructs that terminated at the same residue (e.g. 2638A 1-486 and 2638A 139-486 vs. 2638A 1-411 and 2638A 139-411 suggesting either a consistently favored protein degradation site or a cryptic translational start site.

Example 4

"Shadow" Band Analysis Including Zymogram Analysis

In order to identify the source of the shadow band, it was extracted from the SDS gel [from the full length construct 2638A 1-486 sample], using standard methods and subjected to six cycles of Edman degradation N-terminal protein sequencing (M-SCAN, West Chester, Pa.). The amino acid sequence obtained was MKHIYS (SEQ ID NO:22). The last five residues KHIYS (SEQ ID NO:23), matched perfectly the residues at position 181-184 of the full length 2638A endolysin protein (FIG. 2A), which was consistent with the predicted size of the shadow band from the SDS PAGE (~37 kD) and the N-terminal methionine residue matched the predicted amino acid sequence of a protein expressed from a cryptic translational start site (TTG) at residue 180 thru 486 (36.3 kD), of the published DNA sequence. Codon 180, TTG, is a known translational start codon in *E. coli* (Blattner et al. 1997. *Science* 277:1453-1462) that is present in 2% of *E. coli* genes (Starmer et al., supra). There was not a canonical *E. coli* Shine-Dalgarno (SD) ribosome binding site (UAAG-GAGGU) in the 2638A gene sequences immediate upstream of codon 180, but there is a region of homology to the 3' end of the *E. coli* 16S ribosomal RNA sequence (FIG. 2A) located within the 5-13 nt. pre-cistronic spacing between the SD and translational start codon considered optimal for expression in *E. coli* (Chen et al. 1994. *Nucleic Acids Res.* 22: 4953-4957). These lines of evidence suggested that codon 180 encoded a translational start site.

Figure 2:
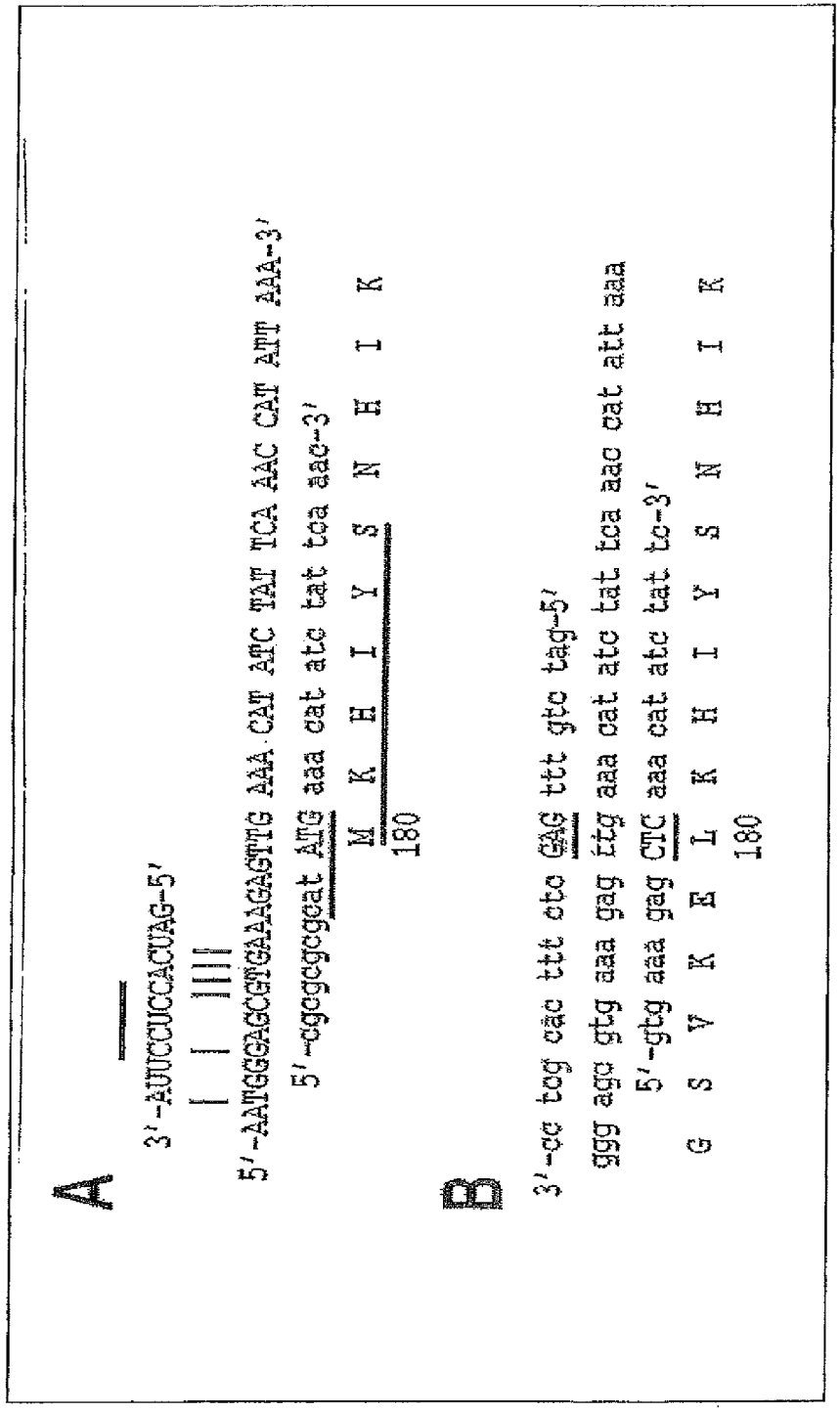
FIGS. 2A and 2B depict DNA and protein sequences near codon 180 of 2638A endolysin, shadow protein, and the 2638A 180-486 construct.

There are similar levels of expression in the SDS PAGE (FIG. 1) for the predicted full length construct and associated shadow bands for four of the constructs (2638A 1-486, 2638A 1-411, 2638A 139-411, 2638A 139-486) where the interdomain sequences included codon 180 (the cryptic TTG translational start site). It was unexpected that expression from the parental pET21a ATG translation start site (commercially optimized for expression with a near consensus *E. coli* SD sequence AGGGAG), would be at a level similar to that of the codon 180 [with a poorly used TTG translational start site and poorly conserved SD sequence (FIG. 2)]. However, it should be remembered that this expression is from a high copy (~40/cell) plasmid and thus expression levels might be near the upper limit of expression possible, such that the expected differences are masked. There was one construct where the interdomain region did not yield similar full length vs. shadow band expression levels 2638A 1-220::3256-486 (FIG. 1). This construct interrupts the amidase domain and thus may have problems achieving a stable tertiary structure in the shadow band resulting in either high instability or the shadow protein being sequestered in inclusion bodies and unavailable via our native protein isolation procedures.

To test the cryptic translational start site hypothesis, a ninth construct with two silent mutations was created where the TTG codon was altered through site-directed mutagenesis to an alternative [CTC] codon that still codes for leucine but did not resemble a translational start site (construct 2638A 1-180Mut-486; FIG. 1A; illustrated in FIG. 2B). To create this construct, a four primer PCR site-directed mutagenesis protocol was used in a protocol described previously (retrieved from the Internet: <URL: csun.edu/~hcbio027/bio-technology/lec5/lec5.html). Mutagenic primers are listed in Table 2 and in FIG. 2B. The PCR fragment harboring the mutation was subcloned into pET21a and sequence verified.

The mutant construct (2638A 1-180Mut-486; FIG. 1A) does not have a shadow band in either the SDS or zymogram gels indicating that our alternative translational start site hypothesis was correct. The single lytic protein product from this construct allowed us to quantify the activity of the full length 2638A endolysin.

In order to test the activity of the amidase domain together with the SH3b cell wall binding domain construct in the absence of the contaminating shadow band protein, we created a construct via PCR cloning that initiated at codon 180 (2638A 180-486; FIG. 1A and described in FIG. 2A). In the SDS PAGE (FIG. 1B), this construct expressed a single major protein band as predicted, and none of the minor contaminating bands contributed to any activity in the zymogram analysis.

The nucleic acid sequences encoding the phage 2638A endolysin-derived proteins: 2638A 1-180 Mut-486, 2638A 139-486, and 2638A 180-486 are identified by SEQ ID NO:1, SEQ ID NO:2, and SEQ ID NO:3, respectively. These sequences include the nucleotides encoding the XhoI cloning site (Leu-Glu) and the six histidine tag required for purification. The amino acid sequence of the phage 2638A endolysin-derived protein 2638A 1-180 Mut-486 is identified by SEQ ID NO:4. The truncated endolysin proteins, 2638A 139-486 and 2638A 180-486 are identified by SEQ ID NO:5 and SEQ ID NO:6, respectively. The recombinant, isolated non-mutated nucleotide sequence (including the nucleotides encoding the XhoI cloning site (Leu-Glu) and the six histidine tag is identified by SEQ ID NO:34. SEQ ID NO:34 encodes the amino acid sequence SEQ ID NO:4.

For Zymogram Analysis: Zymogram gels were loaded (5 µg) and electrophoresed identically. Zymogram contained S. aureus strain Newman, were rinsed in water to remove SDS and soaked in 50 mM Phosphate, 150 mM NaCl, pH 7.5 for 2.5 hours. Lane and predicted molecular weights of each construct: Lane M, Kaleidoscope Molecular Weight Markers (Biorad); Lane 1, 2638A 1-486, 56.6 kD; Lane 2, 2638A 1-196, 23.4 kD; Lane 3, 2638A 1-220, 25.9 kD; Lane 4, 2638A 1-244, 28.6 kD; Lane 5, 2638A 1-220::355-486, 41.25 kD; Lane 6, 2638A 1-411, 48 kD; Lane 7, 2638A 139-411, 32.4 kD; Lane 8, 2638A 139-486, 40.9 kD; Lane 9, 2638A 180-486, 36.3 kD; Lane 10, 2638A 1-180Mut-486, 56.6 kD.

All full length constructs and the shadow bands [except for 2638A 1-220::355-486] showed staphylolytic activity (zones of clearing) in the zymogram (FIG. 1C) indicating: (1) that the N-terminal M23 peptidase domain was enzymatically active with or without the SH3b cell wall binding domain (2638A 1-196; 2638A 1-220; 2638A 1-244; 2638A 1-220::355-486), and (2) the amidase domain was active with or without the full length SH3b domain (2638A 139-411; 2638A 139-486). Zymograms are not usually interpreted quantitatively (especially since these were loaded with µg equivalents and not molar equivalents of enzyme) but rather are used to indicate that the minor contaminating bands in the preparations are not contributing to the activity of the preparation. There was virtually no activity from any of the minor (non-shadow) bands in the zymogram assay after extended periods. However, the presence of nearly equal amounts of the active shadow band (from stained SDS gel) in many preparations negated the ability to quantify the activity from either the isolated amidase domain (2638A 139-411; 2638A 139-486) or the full length construct.

It is apparent from the zymogram that both the M23 peptidase domain and the amidase domain are enzymatically active on SDS treated S. aureus cells.

Example 5

Turbidity Assay

The turbidity assay measures the drop in optical density (OD) resulting from lysis of the target bacteria with the phage endolysin-derived protein. Mid log phase ($OD_{600\ nm}$ of 0.4-0.6) target cells were grown in Brain Heart Infusion (Becton Dickenson, Franklin Lakes, N.J.) and concentrated in lysing buffer A (LBA; 50 mM ammonium acetate, 10 mM $CaCl_2$, 1 mM DTT at pH 6.2) to an $OD_{600\ nm}$ of ~2.0. The turbidity reduction assays were performed with identical molar amounts of proteins and S. aureus strain Newman with the addition of the bivalent metal cations $Mn^{2+}$, $Mg^{2+}$, and $Ca^{2+}$ at a concentration of 1 mM. The turbidity reduction assay contained 0.5 µM protein (5.7 µg of full length repaired construct: 2638A 1-180Mut-486 in 200 µl assay) unless otherwise noted. Lane 1, 2638A 1-486 (5.7 µg total protein in 200 µl assay); Lane 2, 2638A 1-196; Lane 3, 2638A 1-220; Lane 4, 2638A 1-244; Lane 5, 2638A 1-220::355-486; Lane 6, 2638A 1-411; Lane 7, 2638A 139-411; Lane 8, 2638A 139-486; Lane 9, 2638A 180-486; Lane 10, 2638A 1-180Mut-486. Mixing reactions between the repaired full length construct 2638A 1-180Mut-486 (R) and the engineered amidase-SH3b construct 2638A 180-486 (A) were performed in the following ratios Lane 11, R:A::1:1, 1 µM; Lane 12, R:A::1:1, 0.5 µM; Lane 13, R:A::1:3, 0.5 µM; and Lane 14, R:A::3:1, 0.5 µM. Optical Density measurements are taken at regular intervals. If the lysin can digest the cell wall, lysis will occur with a subsequent reduction in OD. Changes in the $OD_{600\ nm}$ in the control sample (cells alone) were subtracted from samples containing both cells and lysin, before calculating the specific activity. Specific Activity=$\Delta OD_{600\ nm}$/µM/min.

The turbidity reduction assay results indicate that the parent full length construct (2638A 1-486), including its shadow band, shows the highest activity in the turbidity reduction assay (FIG. 3) of all constructs. The M23 peptidase domain isolating constructs show minimal activity (2638A 1-196, 2638A 1-220, 2638A 1-244) on live, non-SDS treated S. aureus cells. The full length SH3b domain does not seem to enhance the activity of the M23 peptidase domain (2638A 1-220::355-486), but it appears essential to the activity of the amidase domain, as indicated by the low activity of the 2638A 139-411 construct with a full amidase, but truncated SH3b domain. Activity is also minimal for the M23 peptidase+ amidase dual domain construct lacking the full length SH3b domain (2638A 1-411). These results were verified in a second strain of S. aureus BAC170190 (data not shown). Only in those constructs where there is a full length SH3b domain and the full length amidase domain is there appreciable activity (2638A 139-486, 2638A 180-486, 2638A 1-180Mut-486). The amidase domain appears to be contributing the majority of the lytic activity.

The exact ratio of shadow band:full length construct is unknown as they are produced and purified simultaneously in the nickel column purified preparation. Protein sequence analysis described above indicates that the shadow band produced by the full length construct (2638A 1-486) is the same protein as produced by construct 2638A 180-486. It was reasoned that the protein mixture might be the source of the enhanced activity. To test this hypothesis, a series of mixing experiments were performed where defined molar amounts of both the repaired full length construct (2638A 1-180Mut- 486) and the 2638A 180-486 amidase construct were added in the turbidity reduction assay in an effort to mimic the ratio of full length to shadow band produced by the parent construct (2638A 1-486). Although it is impossible to know the exact concentration of the full length and shadow band in the 2638A 1-486 construct, 0.5 µM of the full length repaired construct is 11 µg of protein. Thus 11 µg of the full length+ shadow band was used in the turbidity reduction assay for comparison. Molar Ratios of 1:1, 1:3 and 3:1 (2638A 1-180Mut-486 repaired: 2638A 180-486 amidase), performed at room temperature (FIG. 3) and after heating the mixtures to 42° C. for one hour (to potentially allow heterodimer formation; data not shown) did not yield activity levels that approached the naturally occurring double band product produced by 2638A 1-486.

There was weak turbidity reduction activity from the 2638A 1-486 parental construct on methicillin resistant *S. aureus* (MRSA) strain (CSA #175, SRCAMB collection) and no activity on *S. epidermidis* (ATCC 14990) (data not shown).

The presence and use of the codon 180 TTG cryptic translational start site in a heterologous *E. coli* expression system begs the question of whether or not this codon 180 translational start site is functional in *S. aureus*. Our results do not address this question specifically, but one study suggests that TTG translational start codons are used in 8% of the *S. aureus* genes examined, a much higher frequency than the 2% of *E. coli* genes cited in the same work (Starmer et al., supra). A search for *S. aureus* SD sequences has identified several: AGAGAG, AGAAAG (Strommenger et al. 2004. *Eur. J. Clin. Microbiol. Infect. Dis.* 23:15-19), GGAGGG (East and Dyke. 1989. *J. Gen. Microbiol.* 135:1001-1015), AAAGGAG (Jones and Khan. 1986. *J. Bacteriol.* 166:29-33) and AAAG-GAAGGAATTA (SEQ ID NO:24; Cuny and Witte. 1996. *J. Clin. Microbiol.* 34: 1502-1505). A cursory comparison of these published sequences to the DNA sequences shown in FIG. 2, immediately 5' to codon 180 [5'-AAAGAATGG-GAGCGTG AAAGA<u>TTG</u>-3' (SEQ ID NO:25)] (codon 180 is underlined) reveals that there are numerous potential/partial binding sites for these staphylococcal SD sequences suggesting that the use of the codon 180 as a translational start site in *S. aureus* is likely.

Turbidity reduction assays suggest that when both the full length and the shadow band protein are putatively produced from the same transcript, there is a heightened endolysin activity derived. If there is a selective advantage to this heightened activity, this might explain why this sequence has been maintained over time.

Thus, the 2638A endolysin is a potent antimicrobial with a uniquely active amidase domain that will be a good addition to future antimicrobial constructs. The 2638A endolysin constructs can be used in novel environments to determine if the unique plate lysis phenotype is predictive of novel environments where this endolysin will find special application.

Example 6

Plate Lysis Assay

Purified proteins for each construct were diluted in sterile nickel column elution buffer, and 6 µL of lysostaphin (11 µg) or the constructs (0.2 nmoles or ~11 µg for the repaired construct 2638A 1-180Mut-486) was spotted onto a freshly spread lawn of *S. aureus* strain NRS119 (SA LinR #12; linezolid resistant) growing cells that had air dried for 30 min on tryptic soy agar (TSA) plates. L=1 µg Lysostaphin (Sigma); Spot 1=11 µg; all other constructs are 0.2 nmoles (~11 µg for the repaired construct 2638A 1-180Mut-486) spotted in 10.

The spotted plates were air dried for 10 min in a laminar flow hood and incubated overnight in a 37° C. environment. Scoring of the cleared spots occurred within 20 h of plating the cells.

The Plate Lysis assay results (FIG. 3) agree with the turbidity reduction assay. Each of the M23 peptidase dependent or SH3b-truncating constructs showing weak activity on *S. aureus* strain Newman strain. In addition to the Plate Lysis results in FIG. 3, we have also examined numerous strains with reduced but real lytic activity (Table 1). However, the plate lysis results with the 2638A endolysin constructs are extremely novel in appearance. Plate lysis results are routinely visualized as a discrete cleared spot on a lawn of bacteria after a single overnight of culture. The cleared zone remains that way for days or weeks, as seen for Lysostaphin in FIG. 3. In contrast, the 2638A endolysin is unique in that sometimes this cleared zone requires multiple days to appear. The 2638A results never show a discrete spot, rather there is a very broad, ill-defined region of clearing that grows with time, up to four days, suggesting that the enzyme is still active for four days and has a heightened diffusion in the media compared to other peptidoglycan hydrolases. This is true with each of the 2638A constructs whether they harbor or lack the SH3b cell wall binding domain, indicating that the 2638A lysin has properties that can make it a unique antimicrobial with staphylolytic properties potentially useful in highly ordered or structured settings e.g. mucosal membranes. These diffusion results indicate that the enzyme is active for several days in the plate, or at least as long as required for the diffusion to occur. Thus, there is also a likelihood that the enzyme might work preferentially on late log or stationary phase cells in the plate lysis assay, as the 3 day old culture is likely not growing as quickly as the freshly-plated overnight culture.

Figure 3:
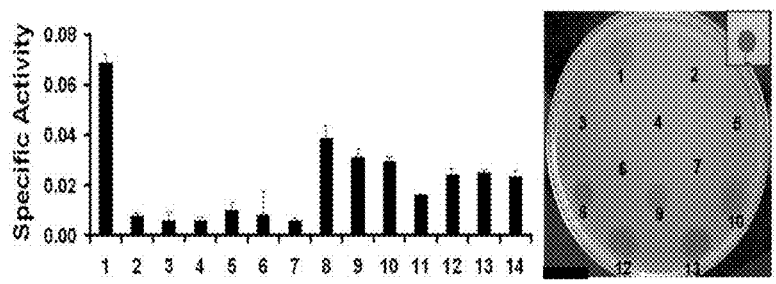
FIG. 3 shows the turbidity reduction and plate lysis assay results of the 2638A constructs. Sample numbering is the same in the turbidity reduction and plate lysis assays. The turbidity reduction assays were performed with identical molar amounts of proteins and S. aureus strain Newman with the addition of the bivalent metal cations $Mn^{2+}$, $Mg^{2+}$, and $Ca^{2+}$ at a concentration of 1 mM. The turbidity reduction assay contained 0.5 µM protein (5.7 µg of full length repaired construct: 2638A 1-180Mut-486 in 200 µl assay) unless otherwise noted. Lane 1, 2638A 1-486 (5.7 µg total protein in 200 µl assay); Lane 2, 2638A 1-196; Lane 3, 2638A 1-220; Lane 4, 2638A 1-244; Lane 5, 2638A 1-220::355-486; Lane 6, 2638A 1-411; Lane 7, 2638A 139-411; Lane 8, 2638A 139-486; Lane 9, 2638A 180-486; Lane 10, 2638A 1-180Mut-486. Mixing reactions between the repaired full length construct 2638A 1-180Mut-486 (R) and the engineered amidase-SH3b construct 2638A 180-486 (A) were performed in the following ratios Lane 11, R:A::1:1, 1 µM; Lane 12, R:A::1:1, 0.5 µM; Lane 13, R:A::1:3, 0.5 µM; and Lane 14, R:A::3:1, 0.5 µM. Optical Density measurements are taken at regular intervals. If the lysin can digest the cell wall, lysis will occur with a subsequent reduction in OD. Specific Activity=$\Delta OD_{600\ nm}$/µM/min. Plate Lysis Assay: S. aureus strain NRS119 (SA LinR #12), linezolid resistant. L=1 µg Lysostaphin (Sigma); Spot 1=11 µg; all other constructs are 0.2 nmoles (~11 µg for the repaired construct 2638A 1-180Mut-486) spotted in 10 µL.

The finding that the 2638A amidase domain is highly active and the M23 peptidase domain appears nearly inactive is unexpected, and in direct opposition to the results of studies with similar proteins, e.g. the staphylococcal LysK (phage K endolysin) and phage phi11 endolysin. Despite a virtually identical protein organization in all three proteins, peptidase-amidase-SH3b, the LysK amidase domain was virtually inactive in constructs where it was isolated, although it was shown to be active in the context of the whole protein (Becker et al. 2009b, supra). Similarly, the phi11 endolysin amidase domain was virtually inactive when isolated in a deletion construct (Sass and Bierbaum. 2007. *Appl. Environ. Microbiol.* 73:347-352). In contrast, the cysteine, histidine-dependent amido-hydrolases/peptidases (CHAP) endopeptidase (Bateman and Rawlings. 2003. *Trends Biochem. Sci.* 28:234-237; Rigden et al. 2003. *Trends Biochem. Sci.* 28:230-234) domain isolating constructs from both the phi11 endolysin (Donovan et al. 2006c., supra; Saas and Bierbaum, supra) and LysK (Becker et al. 2009b, supra; Horgan et al. 2009. *Appl. Environ. Microbiol.* 75:872-874) demonstrate strong lytic activity. Despite readily observed zones of clearing in the zymogram (FIG. 1C), the 2638A M23 peptidase domain constructs show virtually no activity in the turbidity reduction or plate lysis assays (FIG. 3).

Example 7

Control of Systemic MRSA Infection in a Murine Model

Expression and purification of recombinant, C-terminally 6×His-tagged phage endolysins were performed essentially as previously described (Donovan and Foster-Frey, supra), with the following modifications: Induced *E. coli* cultures were harvested, resuspended in 10 mL of lysis buffer (50 mM $NaH_2PO_4$, 300 mM NaCl, 10 mM imidazole, 30% glycerol, pH 8.0) per 1 L culture, and sonicated on ice for 5 min (1 s pulses separated by 1 s rests). After removal of debris by centrifugation (9000×g for 30 min), 6×His-tagged proteins were purified from the cleared supernatant by immobilized metal ion affinity chromatography, using nickel-NTA Superflow resin (QIAGEN, Valencia, Calif.). Purification columns were washed with 25 column volumes (CV) of lysis buffer supplemented with 0.1% Triton X-114 for removal of endotoxins (Reichelt et al. 2006. *Prot. Express. Purif.* 46:483-488), 40 CV of lysis buffer, and 15 CV of wash buffer (50 mM $NaH_2PO_4$, 300 mM NaCl, 20 mM imidazole, 30% glycerol, pH 8.0). Target proteins were eluted with elution buffer (50 mM $NaH_2PO_4$, 300 mM NaCl, 250 mM imidazole, 30% glycerol, pH 8.0) in 500 µl fractions. Fractions with high protein concentrations were combined and dialyzed against Dialysis Buffer (50 mM $NaH_2PO_4$, 300 mM NaCl, 10% glycerol, pH 7.5). Protein concentrations were measured spectrophotometrically using a NanoDrop ND-1000 (NanoDrop Technologies, Wilmington, Del.), and purity was determined via sodium dodecyl sulfate-polyacrylamide gel electrophoresis (SDS-PAGE). Endotoxin concentrations were determined using a Limulus Amoebocyte Lysate (LAL) assay (Lonza, Walkersville, Md.). Endolysin activity was assayed using the plate lysis method essentially as described earlier (Becker et al. 2009b, supra).

Four to six week old female Balb/c mice (weight range 22 g to 24 g, Harlan Laboratories) were used in biosafety level 2 facilities in accordance with IACUC regulations. Briefly, methicillin-resistant *Staphylococcus aureus* (MRSA) strain NRS382, acquired from NARSA (Network on Antimicrobial Resistance in *Staphylococcus aureus*, Chantilly, Va.), was grown at 37° C. overnight in Brain Heart Infusion (BHI) medium (Becton, Dickinson and Company, Sparks, Md.). The culture was then diluted 1:100 and grown to mid-log phase ($OD_{600\ nm}$=0.3-0.4), centrifuged and resuspended in BHI supplemented with 5% mucin (Sigma-Aldrich St Louis, Mo., USA) for the mouse experiment. Mucin functions as immunosuppressant and allows reduction of the bacterial inoculum concentration required to achieve an $LD_{90}$ after 48 hours. Approximately $4 \times 10^7$ CFU bacteria in suspension (in a volume of 0.2 ml) were injected intraperitoneally (I.P.). Actual inoculum titers were derived from plating serial dilutions of each inoculum on BHI agar plates.

Figure 4:
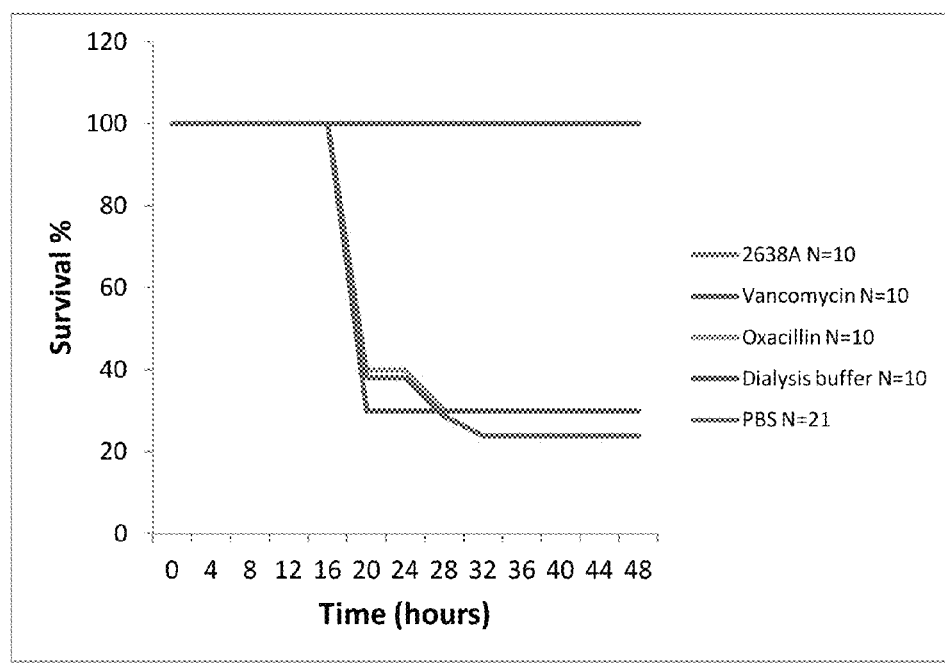
FIG. 4 depicts survival of mice infected intraperitoneally with $4 \times 10^7$ CFU of the MRSA strain NRS382 (NARSA) and treated 30 min post infection.

To determine the in vivo efficacy of 2638A endolysin, 30 minutes post infection, infected mice were divided into several groups (ten mice in each group) and were I.P. injected with 2638A (SEQ ID NO:4) in Dialysis Buffer (200 µg/mouse), or phosphate-buffered saline (PBS) or Dialysis Buffer as controls (0.2 ml/mouse). The antibiotics Vancomycin and Oxacillin (Sigma-Aldrich, St Louis, Mo., USA), prepared in distilled $H_2O$, were used as additional controls. Antibiotics were administrated subcutaneously (Vancomycin: 375 µg/mouse; Oxacillin: 1250 µg/mouse) 30 minutes post infection (FIG. 4 and Table 3).

TABLE 3

In vivo Efficacy of 2638A Endolysin, Oxacillin and Vancomycin.

| | | % Survival | | | |
|---|---|---|---|---|---|
| Hours | PBS | Dialysis Buffer | Oxacillin* | Vancomycin* | 2638A Endolysin* |
| 0 | 100 | 100 | 100 | 100 | 100 |
| 4 | 100 | 100 | 100 | 100 | 100 |
| 8 | 100 | 100 | 100 | 100 | 100 |
| 12 | 100 | 100 | 100 | 100 | 100 |
| 16 | 100 | 100 | 100 | 100 | 100 |
| 20 | 38 | 30 | 40 | 100 | 100 |
| 24 | 38 | 30 | 40 | 100 | 100 |
| 28 | 29 | 30 | 30 | 100 | 100 |
| 32 | 24 | 30 | 30 | 100 | 100 |
| 36 | 24 | 30 | 30 | 100 | 100 |
| 40 | 24 | 30 | 30 | 100 | 100 |
| 44 | 24 | 30 | 30 | 100 | 100 |
| 48 | 24 | 30 | 30 | 100 | 100 |

*N = 10

The survival rate for each experimental group was monitored every 4 hours up to 48 hours post infection. The data were statistically analyzed by Kaplan Meier Survival curves. In addition, a Septicemia Score Index described by Biswas et al. (2002. Infect. Immun. 70:204-210) was used to evaluate the health condition of MRSA-infected mice in intervals of 4 hours for up to 48 hours (Table 4).

TABLE 4

Composite matrix of septicemia.
Composite Matrix of Septicemia

| Score | Disease State | Symptoms |
|---|---|---|
| 0 | Normal | Unremarkable |
| 1 | Slight Illness | Lethargy, Ruffled fur |
| 2 | Moderate Illness | Lethargy, Ruffled fur, Hunched back |
| 3 | Severe Illness | Lethargy, Ruffled fur, Hunched back, Closed eyes/exudate |
| 4 | Moribund | Moribund |
| 5 | Death | Death |

Endolysin 2638A protects mice from MRSA-induced bacteremia. The percentage of mice surviving after intraperitoneal injection of MRSA was monitored for 48 hours. For mice treated with PBS, Dialysis Buffer, or Oxacillin, the survival rate dropped from 100% to less than 40% after 16 to 20 hours, and reached approximately 20% at the end of the experiment (FIG. 4, Table 3). In contrast, 100% of the mice treated with either Vancomycin or the 2638A endolysin, survived until 48 hours post infection.

In order to detect bacteria in the bloodstream, mice surviving until the end of the experiment (48 hours post infection) were euthanized, 100 µl blood samples were taken, mixed with 900 µl of PBS, and then serially diluted and plated on BHI agar plates.

TABLE 5

MRSA recovered* from the bloodstream of infected and treated mice.

| Treatment | Number of mice | Mean NRS382 Titer in the Blood (CFU/ml) |
|---|---|---|
| PBS | 3 | $5.0 \pm 6.2 \times 10^1$ |
| Dialysis Buffer | 1 | $1.4 \times 10^3$ |
| Oxacillin | 3 | $0.9 \pm 1.6 \times 10^3$ |
| Vancomycin | 10 | $1.8 \pm 3.3 \times 10^1$ |
| 2638A | 10 | $0.8 \pm 1.9 \times 10^1$ |

*Recovered 48 hr post infection.

Figure 5:
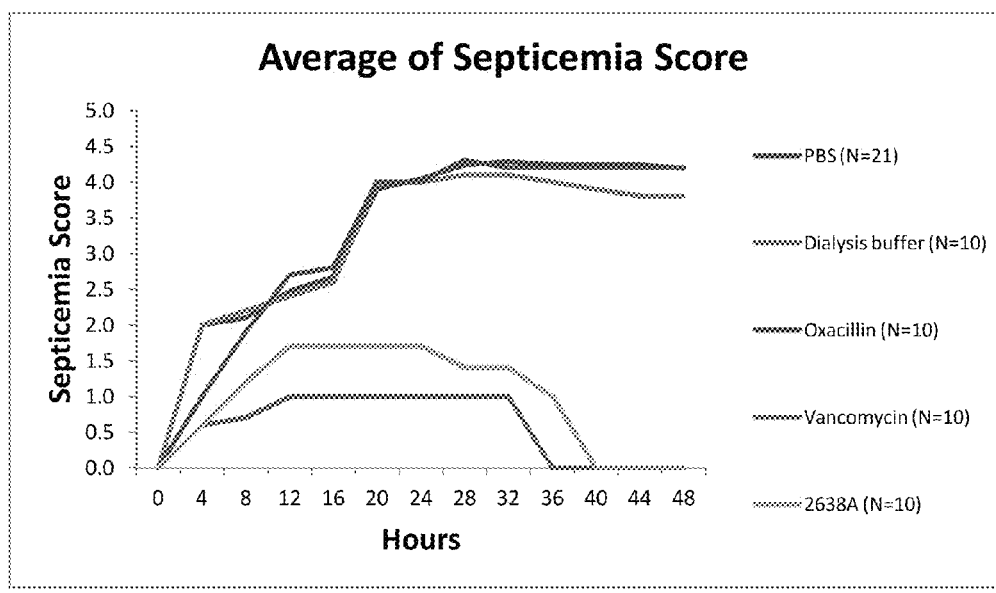
FIG. 5 shows the average septicemia scores of mice infected intraperitoneally with $4 \times 10^7$ CFU of the MRSA strain NRS382 and treated 30 min post infection.

Septicemia scores of animals treated with PBS, Dialysis Buffer, or Oxacillin continuously increased after the treatment and reached an average of approximately 4 (corresponding to a moribund disease state; see Table 4) at 20 hours post infection, which was maintained until the end of the experiment (FIG. 5). In mice treated with either Vancomycin or the 2638A endolysin, average septicemia scores reached a maximum of 1.0 to 1.7 (slight to moderate illness) after approximately 12 hours, which remained stable for 24 hours, followed by rapid recovery of the animals, reflected by a decrease in septicemia scores to 0 at the end of the experiment. Table 5 lists the average numbers of bacteria recovered from the bloodstream of infected and treated animals at the end of the experiment (48 hours). Mice treated with Vancomycin or the 2638A endolysin respond similarly.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated recombinant cDNA construct encoding an antimicrobial peptidoglycan hydrolase enzyme molecule having specificity and exolytic activity for the peptidoglycan cell wall of untreated *Staphylococcus aureus*, wherein said cDNA construct encodes a full length 2638A endolysin-derived peptidoglycan hydrolase comprising a mutation in a codon starting at position 180 of the 2638A endolysin, said 2638A endolysin-derived peptidoglycan hydrolase is 2638A 1-180 Mut-486.

2. The cDNA construct of claim 1 having the sequence SEQ ID NO:1.

3. A cDNA construct of claim 1 wherein said cDNA is in operable linkage to a promoter that drives expression in a host organism.

4. A cloning vector comprising the construct of claim 3.

5. An expression vector comprising the construct of claim 3.

6. An isolated host cell transformed with the cDNA construct according to claim 1.

7. The host cell of claim 6, wherein said host cell is a single-celled organism or a cell of a lower or higher multi-celled organism.

8. A method of making a recombinant peptidoglycan hydrolase protein, said method comprising steps:
   a. introducing into a host cell the cDNA construct of claim 3;
   b. culturing said cell under conditions suitable for expression of said protein; and
   c. recovering the protein so expressed.

* * * * *